(12) United States Patent
Prasad

(10) Patent No.: US 6,673,773 B2
(45) Date of Patent: Jan. 6, 2004

(54) LIGNAN COMPLEX DERIVED FROM FLAXSEED AS HYPERCHOLESTEROLEMIC AND ANTI-ATHEROSCLEROTIC AGENT

(75) Inventor: Kailash Prasad, Saskatoon (CA)

(73) Assignee: University of Saskatchewan Technologies Incorporated, Saskatoon (CA)

( * ) Notice: Subject to any disclaimer, the term of this patent is extended or adjusted under 35 U.S.C. 154(b) by 0 days.

(21) Appl. No.: 10/141,860

(22) Filed: May 10, 2002

(65) Prior Publication Data

US 2003/0212007 A1 Nov. 13, 2003

(51) Int. Cl.⁷ .................. A61K 37/00; C07H 15/00
(52) U.S. Cl. .................. 514/25; 536/4.1; 536/1.1; 536/128; 530/500
(58) Field of Search .................. 514/25; 536/4.1, 536/1.1, 128; 530/500

(56) References Cited

U.S. PATENT DOCUMENTS 5,837,256 A  11/1998  Clark et al. ............. 424/195.1
5,846,944 A  * 12/1998  Prasad
6,264,853 B1 * 7/2001  Westcott et al.

OTHER PUBLICATIONS

MacRae, W. Donald and Towers, G.H. Neil, Biological Activities of Lignans, *Phytochemistry*, vol. 23, No. 6, pp 1207–1220 (1984).

Bakke, Jerome E. and Klosterman, Harold J., Proc. N. Dak. Acad. of Science, 10, 18–22 (1956).

* cited by examiner

*Primary Examiner*—Samuel Barts
*Assistant Examiner*—Michael C. Henry

(57) ABSTRACT

A method is described for treating hypercholesterolemic atherosclerosis or for reducing total cholesterol while raising high-density lipoportoein cholesterol. It involves administering to a patient a substantially pure complex derived from flaxseed and containing secoisolariciresinol diglucoside (SDG), cinnamic acid glucosides and hydroxymethyl glutaric acid.

2 Claims, 5 Drawing Sheets

LIGNAN COMPLEX DERIVED FROM FLAXSEED AS HYPERCHOLESTEROLEMIC AND ANTI-ATHEROSCLEROTIC AGENT

BACKGROUND OF THE INVENTION

1. Field of the Invention

This invention relates to a method for the use of a lignan complex isolated from flaxseed for the treatment of atherosclerosis, e.g. reducing or preventing the development of hypercholesterolemic atherosclerosis, for reducing total cholesterol and for raising HDL-C in blood.

2. Description of the Prior Art

Hypercholesterolemia is a major risk factor for atherosclerosis (narrowing of the artery due to deposition of fat in the arterial wall) and related occlusive vascular diseases such as heart attack, stroke and other peripheral vascular diseases. Heart disease is the number one killer. Hypercholesterolemic atherosclerosis has been reported to be associated with oxidative stress increase in levels of reactive oxygen species (ROS), production of ROS by polymorphonuclear leukocytes as assessed by chemiluminescence (PMNL-CL), and a decrease in the antioxidant reserve. Pretreatment with antioxidants (vitamin E, probucol, garlic, purpurogallin, secoisolariciresinol diglucoside) reverses the effects of hypercholesterolemia. Flaxseed which is a rich source of $\alpha$-linolenic acid and richest source of plant lignans has been shown to be effective in reducing hypercholesterolemic atherosclerosis without lowering serum levels of cholesterol. Using flaxseed which has very low $\alpha$-linolenic acid, has shown that antiatherogenic activity of flaxseed is not due to $\alpha$-linolenic acid but may be due to lignan component of flaxmeal.

Presently the treatment of hypercholesterolemia and hypercholesterolemic atherosclerosis is to reduce hypercholesterolemia by using various lipid lowering agents such as bile acid sequestrant (cholestyramine, colestipol), nicotinic acid, HMG-CoA reductase inhibitor (lovastatin, provastatin, simvastatin, fluvastatin and atrovastatin) and gemfibrozil. Recently probucol which has both antioxidant and lipid lowering activity and vitamin E which has antioxidant activity have been used to prevent atherosclerosis and restenosis.

Drugs used for lowering serum lipids and for treatment of atherosclerosis (heart attack and stroke) have many side effects and are expensive. Fibric acid derivatives (gemfibrozil) produces gall stones, myopathy and hepatomegaly. Nicotinic acid produces gastrointestinal symptoms, flushing, hyperglycemia, hepatic dysfunction, elevated uric acid, abnormal glucose tolerance, and skin rash. Bile acid sequestrant (cholestyramine, colestipol) produces gastrointestinal symptoms, and high serum levels of very low density-lipoprotein (VLDL). HMG-CoA reductase inhibitors (statin) produce gastrointestinal symptoms, myopathy and hepatotoxicity. Probucol produces diarrhea and decreases the serum levels of HDL (good cholesterol).

Prasad, U.S. Pat. No. 5,846,944, describes the use of secoisolariciresinol diglucoside (SDG), isolated from flaxseed, for reducing hypercholesterolemic atherocleorsis and reducing serum cholesterol. However, isolating SDG from flaxseed is a relatively expensive procedure.

In Westcott et al., U.S. Pat. No. 6,264,853, a new lignan complex is described which has been isolated from flaxseed. This lignan complex typically contains SDG (35%), cinnamic acid glycosides and hydroxymethyl glutaric acid. Only a simple procedure is required to isolate this lignan complex from flaxseed.

The purpose of the present invention is to provide a method of using the above lignan complex derived from flaxseed for medical purposes.

SUMMARY OF THE INVENTION

In accordance with this invention, it has been found that a lignan complex isolated from flaxseed can safely be administered to humans or non-human animals for the treatment of a variety of diseases. The complex and a method for its production are described in Westcott et al., U.S. Pat. No. 6,264,853, issued Jul. 24, 2001, and incorporated herein by reference. This complex is used in substantially pure form, e.g. a purity of at least 95%, and contains secoisolariciresinol diglucoside (SDG), cinnamic acid glucosides and hydroxymethyl glutaric acid. It typically has a nominal molecular weight in the range of about 30,000 to 100,000. The complex can be administered orally or intraperitoneally and has been found to be highly effective when administrated in a daily oral dosage of 20 to 60 mg per kg of body weight. The oral doses may conveniently be in the form of tablets or capsules and the complex may be used together with a variety of pharmaceutically acceptable diluents or carriers.

When administered to humans or non-human animals, the complex has been found to be highly effective for treating hypercholesterolemic atherosclerosis, as well as for reducing total cholesterol and raising HDL-C in blood. Thus, it is useful for the prevention and treatment of coronary artery disease, stroke and other peripheral vascular diseases.

In the graphs, the results are expressed as mean±S.E. The symbols used in FIGS. 1 to 5 have the following meanings.

*P<0.05, Comparison of values at different times with respect to time "0" in the respective group.

[a]P<0.05, Control vs other groups.

[b]P<0.05, Lignan complex vs 0.5% cholesterol or 0.5% cholesterol+lignan complex.

[c]P<0.5, 0.5% Cholesterol vs 0.5% cholesterol+lignan complex.

[+]P<0.05, Month 1 vs month 2 in the respective groups.

Figure 7:
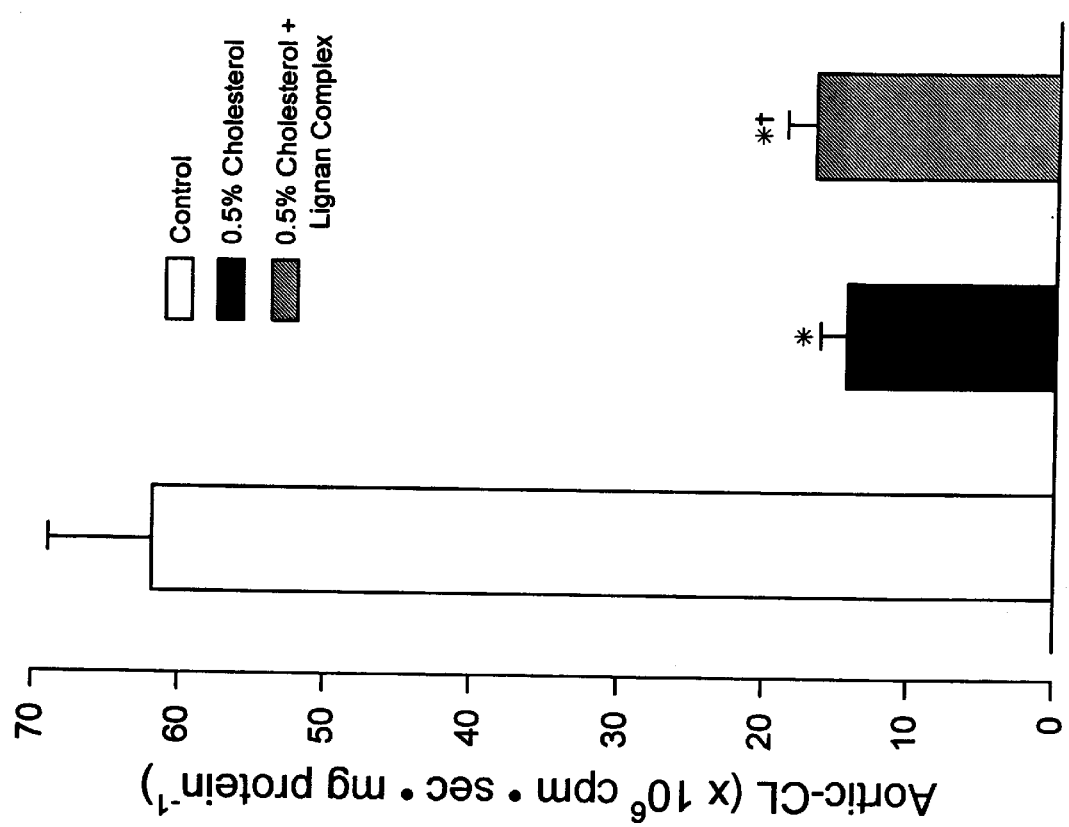
FIG. 7 is a bar graph showing aortic tissue chemiluminescence (Aortic-CL) for three different experimental groups.
Figure 6:
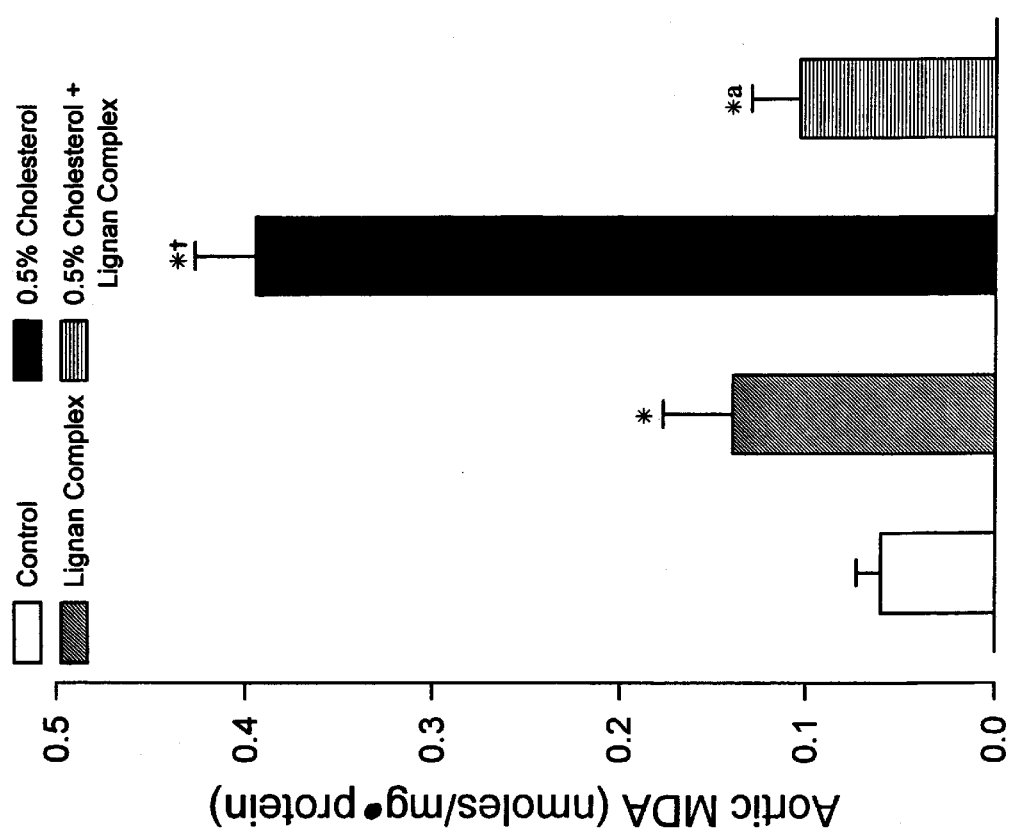
FIG. 6 is a bar graph showing aortic tissue malondialdehyde (MDA) concentration for four different experimental groups.

In FIGS. 6 and 7 the symbols have the following meanings:

*P<0.05, control Vs other groups; †P<0.05, lignan complex Vs 0.5% cholesterol or 0.5% cholesterol+lignan complex.

[a]P<0.05, 0.5% cholesterol Vs 0.5% cholesterol+lignan complex.

For FIG. 7, the significance symbols are as follows:

*P<0.05, control Vs other groups.

†P<0.05, 0.5% cholesterol Vs 0.5% cholesterol+lignan complex.

DESCRIPTION OF THE PREFERRED EMBODIMENTS

The complex used according to this invention typically contains about 34 to 37% by weight of SDG, about 15 to 21% by weight cinnamic acid glucosides and about 9.6 to 11.0% by weight hydroxymethyl glutaric acid. The cinnamic acid glycosides include coumaric acid glucoside and ferulic acid glucoside. They are typically present in the complex in amounts of about 9.5 to 16.0% by weight coumaric acid glucoside and 4.5 to 5.0% ferulic acid glucoside.

The complex composition typically contains about 59 to 70% by weight of the above active ingredients. The balance comprises protein, ash and water of crystallization.

The invention is further illustrated by the following non-limiting examples.

EXAMPLE 1

EXPERIMENTAL PROTOCOL

Experiments were conducted on New Zealand White rabbits. Rabbits were assigned to 4 groups as shown in Table 1. Those in Group I were fed rabbit laboratory chow diet. The other groups received lignan complex or cholesterol or cholesterol+lignan complex. The lignan complex was obtained from Agriculture and Agri-Food Canada and was extracted from flaxseed by the method described in Westcott et al., U.S. Pat. No. 6,264,853 incorporated herein by reference. The diet was especially prepared by Purina and did not contain any antioxidant. Lignan complex was given orally daily in the dose of 40 mg/kg body weight. The rabbits were cared for according to approved standards for laboratory animal care. The rabbits were on their respective diet treatment for 2 months.

Blood samples were collected (from ear marginal artery) for measurement of serum-triglycerides (TG), total cholesterol. (C), low-density lipoprotein cholesterol (LDL-C), high-density lipoprotein cholesterol (HDL-C), enzymes, albumin, creatinine, and malondialdehyde (MDA) before (0 time) and after 1 and 2 months on the respective experimental diets. The rabbits were anesthetized at the end of 2 months and aortas were removed for assessment of atherosclerotic plaques, and measurement of aortic tissue MDA and antioxidant reserve (Aortic-chemiluminescence). The measurement of lipids, atherosclerotic plaques, oxidative stress were done according to known methods. Serum enzymes, albumin and creatinine for assessment of liver and kidney function were measured by already established techniques. Assessment of hemopoietic system were made by established techniques available in the hospital.

SERUM LIPIDS. Changes in serum TG, C, LDL-C, and HDL-C in the 4 groups are shown in FIGS. 1–4. Lignan complex did not affect serum TG, TC, LDL-C but increased HDL-C significantly in the groups on control diet. A 0.5% cholesterol diet increased serum TG, C, LDL-C and HDL-C. Lignan complex in 0.5% cholesterol-fed rabbit produced less increase in C and LDL-C, and greater increase in HDL-C as compared to only 0.5% cholesterol-fed rabbits. Serum TG levels were similar in Group III and IV.

These results indicate that the lignan complex lowers serum cholesterol (significantly) and LDL-C (not significant), and raises HDL-C (significantly) in hypercholesterolemic rabbit. Lignan complex also raises HDL-C in normocholesterolemic rabbits.

Figure 2:
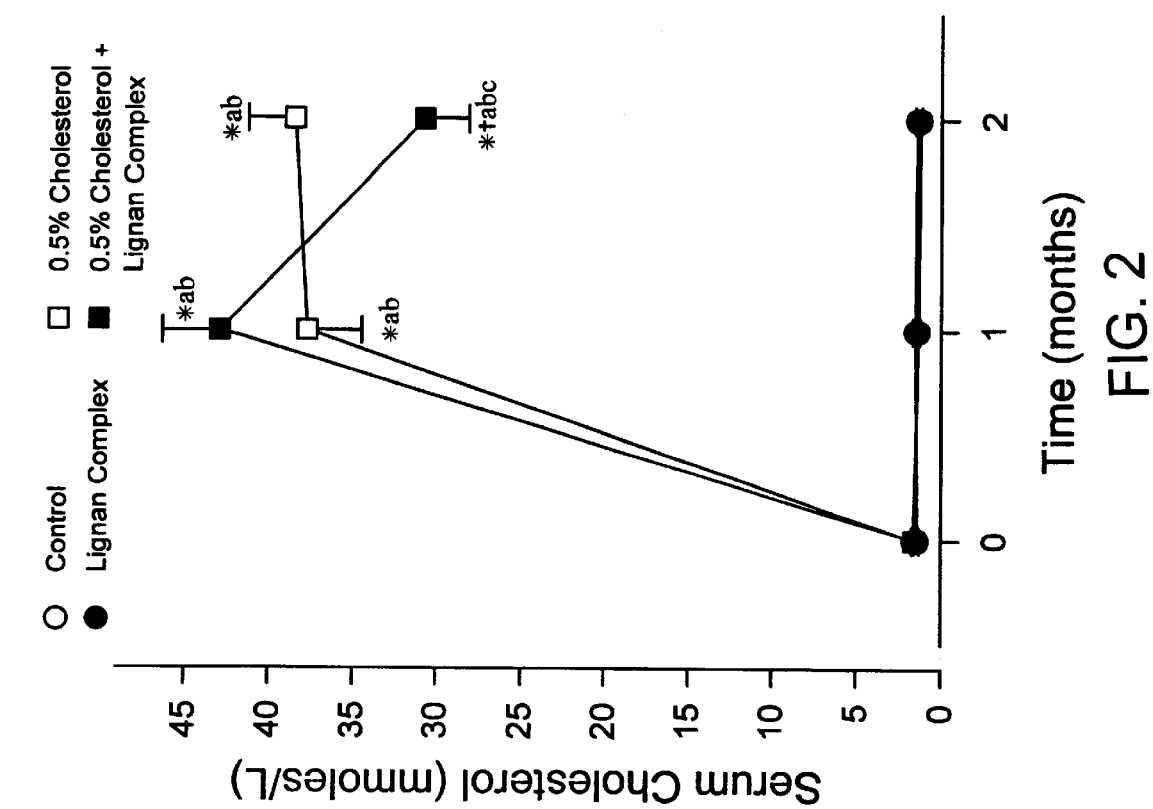
FIG. 2 is a graph showing sequential changes in serum total cholesterol concentration of four different experimental groups.
Figure 1:
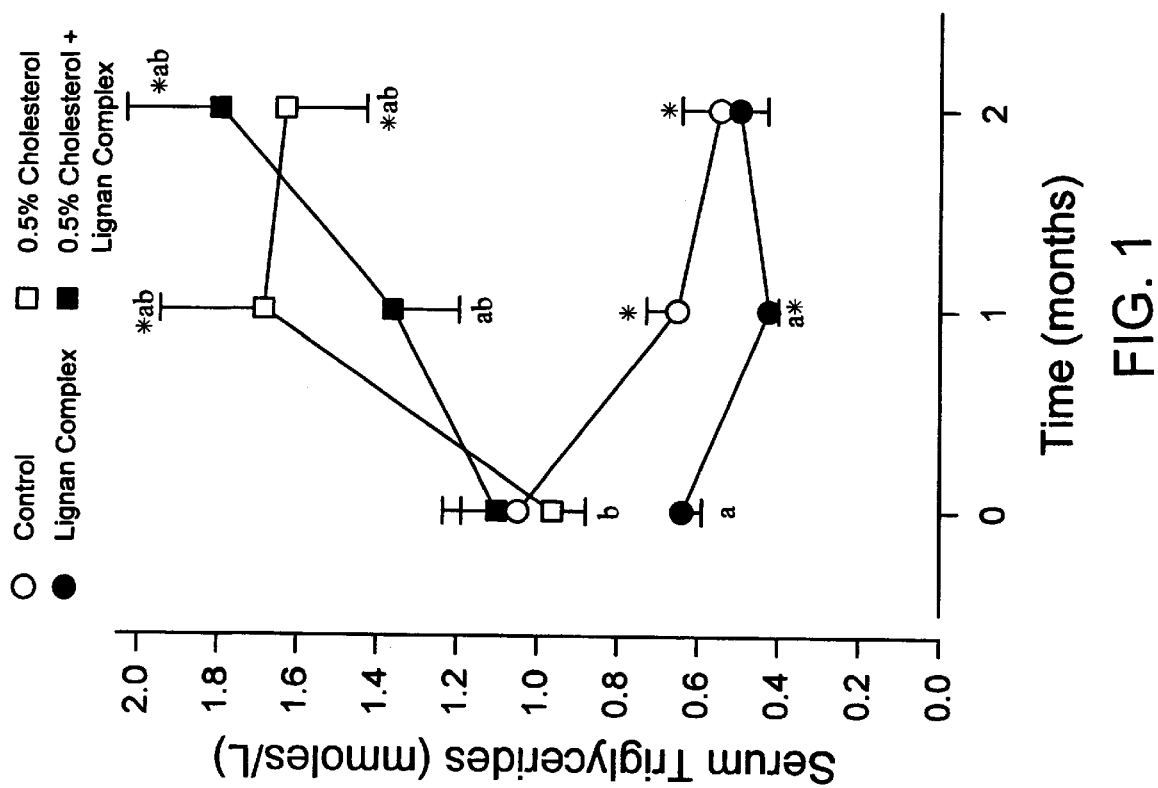
FIG. 1 is a graph showing sequential changes in serum triglyceride concentration for four different experimental groups.
Figure 4:
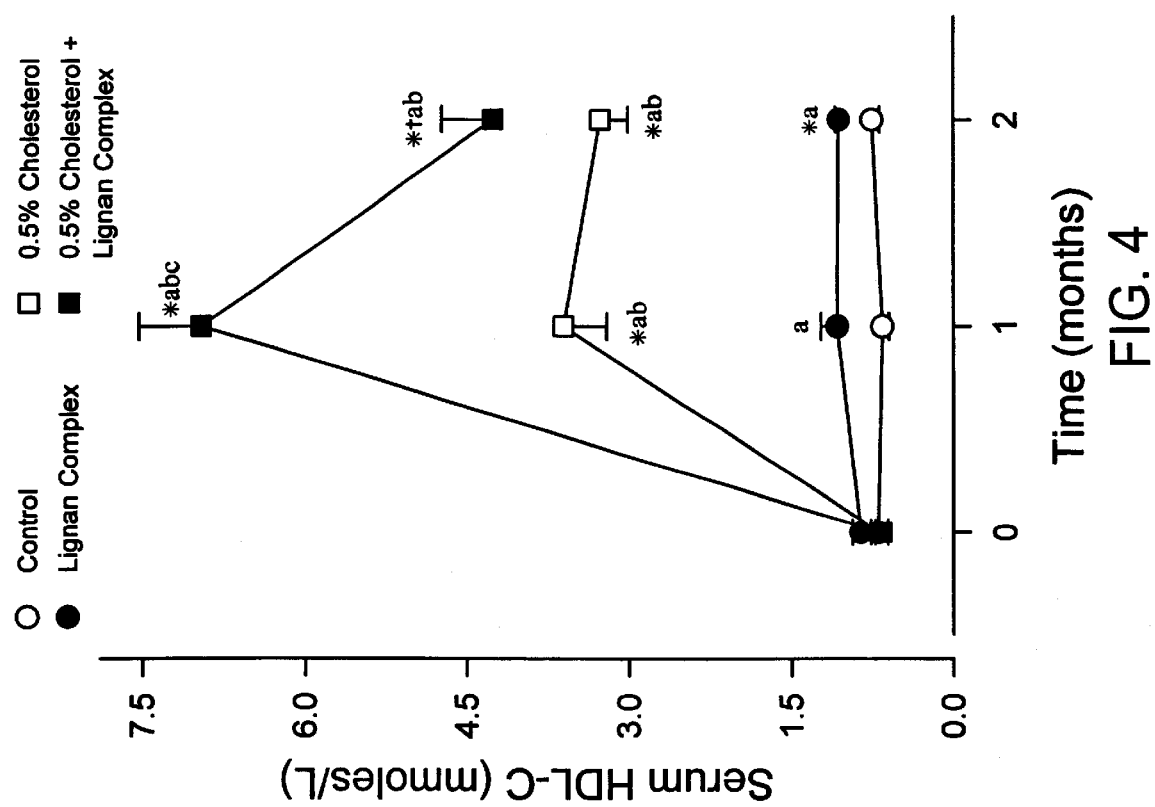
FIG. 4 is a graph showing sequential changes in serum HDL-C concentration for four different experimental groups.
Figure 3:
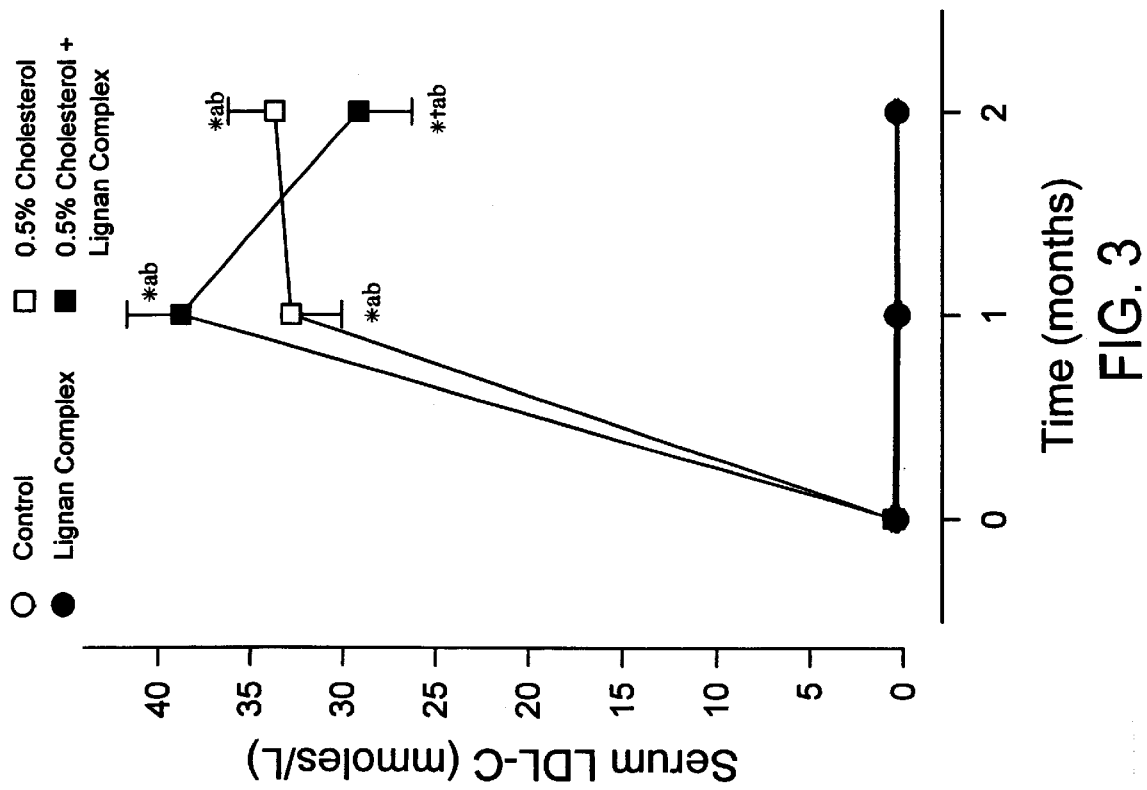
FIG. 3 is a graph showing sequential changes in serum LDL-C concentration for four different experimental groups.
Figure 5:
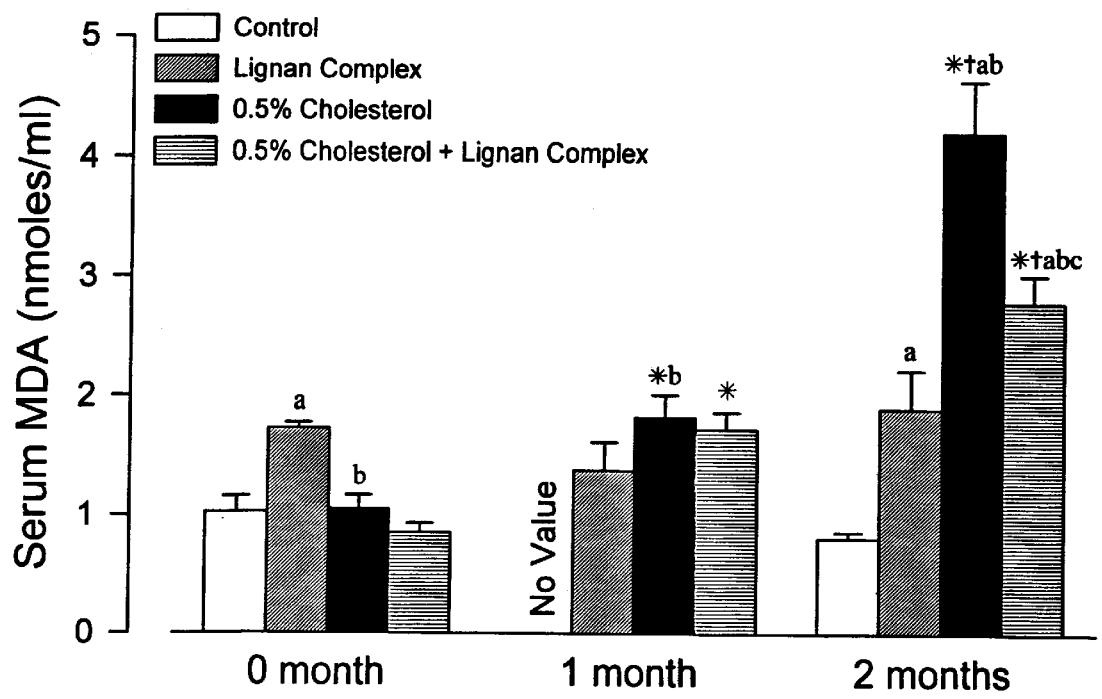
FIG. 5 is a bar graph showing sequential changes in serum malondialdehyde (MDA) for four different experimental groups.

OXIDATIVE STRESS. Results for oxidative stress parameters (serum MDA, aortic tissue-MDA, aortic tissue antioxidant reserve) are shown in FIGS. 5–7. Serum MDA levels remained unaltered in control and lignan complex groups. It increased in both 0.5% cholesterol and 0.5% cholesterol+lignan groups. However, the increase was less in groups with 0.5% cholesterol+lignan complex. Aortic MDA increased and lignan complex decreased in 0.5% cholesterol-fed rabbits. Aortic tissue chemiluminscence (Aortic-CL) is a measure of antioxidant reserve. An increase in Aortic-CL suggests a decrease in the antioxidant reserve and vice-versa. Aortic-CL decreased in cholesterol-fed group of rabbits. Lignan complex in cholesterol-fed rabbits tended to increase the aortic-CL compared to 0.5% cholesterol without lignan complex.

These results indicate that high cholesterol increases oxidative and the lignan complex reduces oxidative stress.

Figure 9:
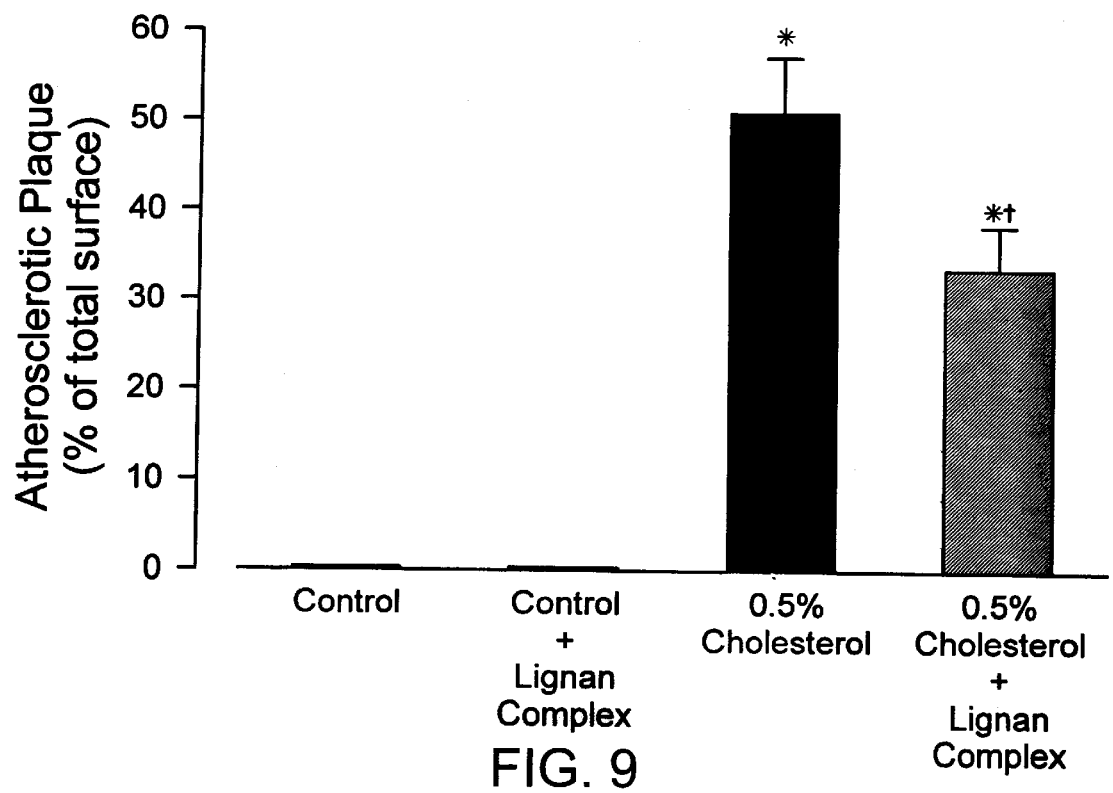
FIG. 9 is a bar graph showing the extent of atherosclerotic plaques in the initial surface of aorta for four different experimental groups.
Figure 8:
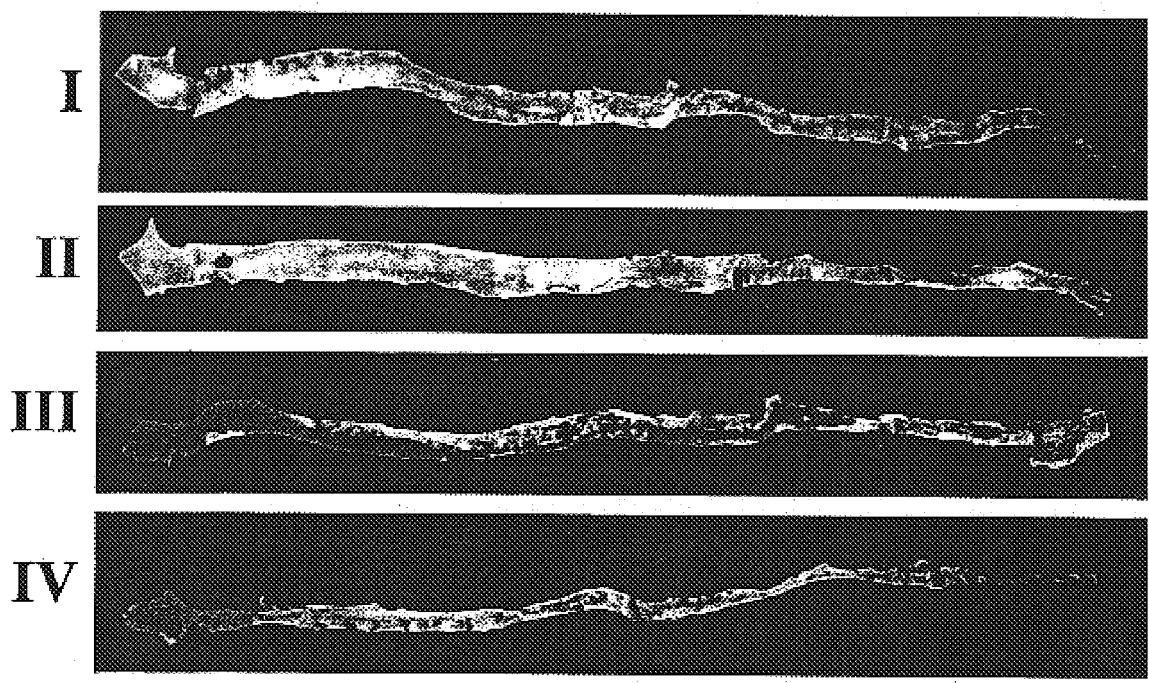
FIG. 8 shows photographs of endothelial surfaces of aortas for four different experimental groups.

ATHEROSCLEROSIS. Representative photographs of endothelial surfaces of aortas from each group are depicted in FIG. 8, and the results are summarized in FIG. 9. In FIG. 8, Group I is Control, Group II is lignan complex, Group III is 0.5% cholesterol and Group IV is 0.5% cholesterol+lignan complex. In FIG. 9:

*P<0.05 Group I or Group II vs Group III and Group IV.

†P<0.05, Group III vs Group IV.

Atherosclerotic plaques were absent in Group I and II. However, a significant area of aortic surface from Group III (50.84±6.23%) and Group IV (33.40±4.80%) was covered with atherosclerotic plaques.

This indicates that the lignan complex reduced the hypercholesterolemic atherosclerosis by 34.3%.

HEMOPOIETIC SYSTEM

Red Blood Cells (RBCs). The changes in various parameters related to RBC are shown in Tables 2–8. In general lignan complex in the control diet group (Group II) did not affect the RBC count, hemoglobin (Hb), hematocrit (Hct), mean corpuscular volume (MCV), mean corpuscular hemoglobin (MCH), mean corpuscular hemoglobin concentration (MCHC) and red blood cell distribution width (RDW). Cholesterol diet (Group III) alone produced significant decreases in RBC, Hb, Hct and MCH; increases in RDW; and no change in MCV and MCHC. Lignan complex in 0.5% cholesterol-fed rabbits (Group IV) reduced RBC, Hb, and Hct; increased MCV, MCH and RDW. The values for RBC, Hb, Hct, MCV, MCH, MCHC and RDW in Group IV were not significantly different from those in Group III. This shows that, in general, the lignan complex has no adverse effects on the hemopoietic system.

White Blood Cells. The changes in the white blood cells (WBCs) and the differential counts granulocytes, lymphocytes, and monocytes are shown in Tables 9–12. Lignan complex in the control diet group (Group II) produced decreases in WBCs and monocytes, and no changes in granulocytes and lymphocytes. These changes in the various parameters in Group II were not significantly different from those in control group (Group I). These parameters of WBCs were unaffected in Group III and IV except in Group III where monocyte counts decreased.

These results indicate that lignan complex has no adverse effects on the WBCs, granulocytes, lymphocytes and monocyte counts.

PLATELET. The changes in platelet counts and mean platelet volume (MPV) of the four groups are summarized in Tables 13–14. Platelet counts slightly decreased in Group I but MPV remained unchanged. These parameters remained unaltered in Group II. Basically, all the parameters in all the groups remained unaltered. These results indicate that lignan complex has no adverse effects on platelet counts and mean platelet volume.

EXAMPLE 2

Studies were conducted to determine if the lignan complex given for 2 months produces adverse effects on liver and kidney function.

(a) Assessment of liver function was made by measuring serum enzymes [alkaline phosphatase (ALP), alanine amino-transferase (ALT), aspartate aminotransferase (AST) and gamma-glutamyltransferase (GGT)] and serum albumin. These serum enzymes are elevated and serum albumin is decreased in liver disease. The results are summarized in Table 15–19. Serum levels of ALT, AST and GGT were similar in Groups I and II at month two of the protocol, however levels of serum ALP were lower in Group II compared to Group I. The changes in the serum levels of ALP, ALT and GGT remained unchanged as compared to "0" month in the Groups III and IV. However serum levels of AST increased to a similar extent in both groups III and IV. Serum albumin levels increased at month one as compared to "0" month in all the groups, however the increases at month two were not significantly different as compared to "0" month. The values of serum albumin at month two, although higher in Groups I and II as compared to Group III and IV, they were not significantly different from each other.

These results indicate that hypercholesterolemia has adverse effects on liver function and that the lignan complex does not have adverse effects on liver function.

(b) Assessment of kidney function was made by measuring serum enzymes (ALT and AST) and creatinine. ALT, AST and creatinine levels are elevated in dysfunctional kidney. The results are summarized in Tables 16, 17 and 20.

There were no significant differences in the values of serum ALT, AST and creatinine among the 4 groups.

These results indicate that the lignan complex or hypercholesterolemia did not have adverse effects on kidney function.

EXAMPLE 3

The lignan complex was also fed orally to normal ratsfor 2 months at a daily dosage of 40 mg/kg of body weight and the rats were studied to see if the complex had any affect on the liver and kidney function and hemopoietic cells. It was found that the lignan complex did not affect any of the above, indicating that it is not toxic to liver, kidney and blood cells.

TABLE 1

Experimental Diet Groups

| Group | Diet/Treatment |
|---|---|
| I (n = 10) | Control (Rabbit chow diet) |
| II (n = 6) | Lignan complex control (Rabbit chow diet supplemented with lignan complex, 40 mg/kg body weight, orally, daily) |
| III (n = 12) | Cholesterol diet (0.5% cholesterol in rabbit chow diet) |
| IV (=16) | Cholesterol diet + lignan complex (0.5% cholesterol diet supplemented with lignan complex, 40 mg/kg; body weight, orally, daily) |

TABLE 2

Red Blood Cells (RBC) Counts ($10^{12}$/L) in the Experimental Groups

| | Time (months) | | |
|---|---|---|---|
| Group | 0 | 1 | 2 |
| I. Control diet | 5.08 ± 0.12 | 6.22 ± 0.18* | 6.04 ± 0.16* |
| II. Control diet + lignan complex | 5.76 ± 0.16$^a$ | 6.03 ± 0.13 | 5.90 ± 0.20 |
| III. 0.5% cholesterol diet | 5.67 ± 0.07$^a$ | 5.61 ± 0.09$^{a,b}$ | 4.60 ± 0.11*$^{,\dagger,a,b}$ |
| IV. 0.5% cholesterol diet + lignan complex | 5.83 ± 0.09$^a$ | 5.43 ± 0.06*$^{,a,b}$ | 4.70 ± 0.14*$^{,\dagger,a,b}$ |

*P < 0.05, 0 month vs 1 and 2 months in the respective groups.
$^\dagger$P < 0.05, 1 month vs 2 months in the respective group.
$^a$P < 0.05, Group I vs other groups.
$^b$P < 0.05, Group II vs Group III or Group IV.

TABLE 3

Hemoglobin Levels in the Blood (g/L) in the Experimental Groups

| | Time (months) | | |
|---|---|---|---|
| Group | 0 | 1 | 2 |
| I. Control diet | 111.8 ± 1.6 | 133.8 ± 4.2* | 128.9 ± 2.5* |
| II. Control diet + lignan complex | 126.8 ± 2.2$^\dagger$ | 134.6 ± 2.4* | 129.0 ± 3.1 |
| III. 0.5% cholesterol diet | 125.1 ± 1.6$^\dagger$ | 122.8 ± 1.7$^{\dagger,a}$ | 107.7 ± 2.2*$^{,\dagger,a}$ |
| IV. 0.5% cholesterol diet + lignan complex | 127.6 ± 1.6$^\dagger$ | 122.9 ± 1.8$^{\dagger,a}$ | 110.0 ± 2.6*$^{,\dagger,a}$ |

*P < 0.05, 0 month vs 1 and 2 months in the respective groups.
$^\dagger$P < 0.05, 1 month vs 2 months in the respective group.
$^a$P < 0.05, Group I vs other groups.
$^b$P < 0.05, Group II vs Group III or Group IV.

TABLE 4

Hematocrit (L/L) in the Experimental Groups

| | Time (months) | | |
|---|---|---|---|
| Group | 0 | 1 | 2 |
| I. Control diet | 0.327 ± 0.00 | 0.385 ± 0.01* | 0.376 ± 0.01* |
| II. Control diet + lignan complex | 0.357 ± 0.00$^a$ | 0.382 ± 0.01* | 0.373 + 0.01 |
| III. 0.5% cholesterol diet | 0.364 ± 0.01$^a$ | 0.348 ± 0.01*$^{,a,b}$ | 0.300 ± 0.01*$^{,\dagger,a,b}$ |

TABLE 4-continued

Hematocrit (L/L) in the Experimental Groups

| Group | Time (months) | | |
|---|---|---|---|
| | 0 | 1 | 2 |
| IV. 0.5% cholesterol diet + lignan complex | 0.372 ± 0.00[a] | 0.347 ± 0.01*,[a,b] | 0.310 ± 0.01*,†,[a,b] |

*$P < 0.05$, 0 month vs 1 and 2 months in the respective groups.
†$P < 0.05$, 1 month vs 2 months in the respective group.
[a]$P < 0.05$, Group I vs other groups.
[b]$P < 0.05$, Group II vs Group III or Group IV.

TABLE 5

Mean corpuscular volume (fL) in the Experimental Groups

| Group | Time (months) | | |
|---|---|---|---|
| | 0 | 1 | 2 |
| I. Control diet | 64.4 ± 0.9 | 61.8 ± 0.9 | 62.3 ± 0.9 |
| II. Control diet + lignan complex | 62.4 ± 1.1 | 63.4 ± 1.0 | 63.3 ± 0.8 |
| III. 0.5% cholesterol diet | 64.2 ± 0.4 | 62.2 ± 0.4* | 65.3 ± 0.5†,[a] |
| IV. 0.5% cholesterol diet + lignan complex | 63.8 ± 0.6 | 64.0 ± 0.6[c] | 66.1 ± 0.6*,†,[a,b] |

*$P < 0.05$, 0 month vs 1 and 2 months in the respective groups.
†$P < 0.05$, 1 month vs 2 months in the respective group.
[a]$P < 0.05$, Group I vs other groups.
[b]$P < 0.05$, Group II vs Group III or Group IV.
[c]$P < 0.05$, Group III vs Group IV.

TABLE 6

Mean Corpuscular Hemoglobin (pg) in the Experimental Groups

| Group | Time (months) | | |
|---|---|---|---|
| | 0 | 1 | 2 |
| I. Control diet | 22.0 ± 0.34 | 21.5 ± 0.26 | 21.4 ± 0.32 |
| II. Control diet + lignan complex | 22.1 ± 0.38 | 22.4 ± 0.33 | 21.9 ± 0.34 |
| III. 0.5% cholesterol diet | 22.1 ± 0.15 | 22.0 ± 0.24 | 23.4 ± 0.20*,†,[a,b] |
| IV. 0.5% cholesterol diet + lignan complex | 21.9 ± 0.26 | 22.7 ± 0.19*,[a,c] | 23.4 ± 0.23*,†,[a,b] |

*$P < 0.05$, 0 month vs 1 and 2 months in the respective groups.
†$P < 0.05$, 1 month vs 2 months in the respective group.
[a]$P < 0.05$, Group I vs other groups.
[b]$P < 0.05$, Group II vs Group III or Group IV.
[c]$P < 0.05$, Group III vs Group IV.

TABLE 7

Mean Corpuscular Hemoglobin Concentration (g/L) in the Experimental Groups

| Group | Time (months) | | |
|---|---|---|---|
| | 0 | 1 | 2 |
| I. Control diet | 341.8 ± 3.8 | 347.6 ± 1.8 | 343.3 ± 1.5 |
| II. Control diet + lignan complex | 354.2 ± 1.7 | 352.5 ± 1.7 | 346.2 ± 2.4* |
| III. 0.5% cholesterol diet | 343.5 ± 1.5 | 351.7 ± 2.5 | 357.7 ± 1.9 |

TABLE 7-continued

Mean Corpuscular Hemoglobin Concentration (g/L) in the Experimental Groups

| Group | Time (months) | | |
|---|---|---|---|
| | 0 | 1 | 2 |
| IV. 0.5% cholesterol diet + lignan complex | 342.9 ± 2 | 354.6 ± 3.0 | 354.9 ± 1.7 |

*$P < 0.05$, 0 month vs 1 and 2 months in the respective groups.

TABLE 8

Red Blood Cell Distribution Width (RDW) as % in the Experimental Groups

| Group | Time (months) | | |
|---|---|---|---|
| | 0 | 1 | 2 |
| I. Control diet | 11.68 ± 0.22 | 12.44 ± 0.37 | 12.84 ± 0.35 |
| II. Control diet + lignan complex | 13.52 ± 0.28[a] | 13.1 ± 0.33 | 12.95 ± 0.32 |
| III. 0.5% cholesterol diet | 11.56 ± 0.20[b] | 12.3 ± 0.14*,[b] | 13.42 ± 0.3*,† |
| IV. 0.5% cholesterol diet + lignan complex | 12.2 ± 0.27[b] | 13.1 ± 0.29*,[c] | 13.17 ± 0.21* |

*$P < 0.05$, 0 month vs 1 and 2 months in the respective groups.
†$P < 0.05$, 1 month vs 2 months in the respective group.
[a]$P < 0.05$, Group I vs other groups.
[b]$P < 0.05$, Group II vs Group III or Group IV.
[c]$P < 0.05$, Group III vs Group IV.

TABLE 9

White Blood Cell Counts ($10^9$/L) in the Experimental Groups

| Group | Time (months) | | |
|---|---|---|---|
| | 0 | 1 | 2 |
| I. Control diet | 4.96 ± 0.62 | 5.34 ± 0.77 | 5.3 ± 0.38 |
| II. Control diet + lignan complex | 7.7 ± 0.7[a] | 7.33 ± 0.25[a] | 4.85 ± 0.78*,† |
| III. 0.5% cholesterol diet | 6.34 ± 0.33 | 8.5 ± 0.48*,[a] | 6.88 ± 0.73 |
| IV. 0.5% cholesterol diet + lignan complex | 6.05 ± 0.28[b] | 9.14 ± 0.44*,[a,b] | 6.59 ± 0.93† |

*$P < 0.05$, 0 month vs 1 and 2 months in the respective groups.
†$P < 0.05$, 1 month vs 2 months in the respective group.
[a]$P < 0.05$, Group I vs other groups.
[b]$P < 0.05$, Group II vs Group III or Group IV.

TABLE 10

Granulocytes Content of Blood ($10^9$/L) in the Experimental Groups

| Group | Time (months) | | |
|---|---|---|---|
| | 0 | 1 | 2 |
| I. Control diet | 0.96 ± 0.12 | 0.64 ± 0.08 | 1.02 ± 0.15 |
| II. Control diet + lignan complex | 1.14 ± 0.18 | 1.21 ± 0.08[a] | 0.65 ± 0.09† |
| III. 0.5% cholesterol diet | 1.10 ± 0.08 | 1.75 ± 0.27*,[a] | 1.36 ± 0.23 |

TABLE 10-continued

Granulocytes Content of Blood ($10^9$/L) in the Experimental Groups

| | Time (months) | | |
|---|---|---|---|
| Group | 0 | 1 | 2 |
| IV. 0.5% cholesterol diet + lignan complex | 0.87 ± 0.078 | 1.21 ± 0.20 | 1.84 ± 0.38* |

*$P < 0.05$, "0" time vs 1 month and 2 months in the respective groups.
†$P < 0.05$, 1 month vs 2 months in the respective group.
[a]$P < 0.05$, Group I vs other groups.

TABLE 11

Lymphocyte Counts in Blood ($10^9$/L) in the Experimental Groups

| | Time (months) | | |
|---|---|---|---|
| Group | 0 | 1 | 2 |
| I. Control diet | 3.42 ± 0.44 | 4.22 ± 0.69 | 4.0 ± 0.29 |
| II. Control diet + lignan complex | 5.27 ± 0.33[a] | 5.53 ± 0.27[a] | 3.87 ± 0.65† |
| III. 0.5% cholesterol diet | 4.19 ± 0.19[b] | 6.41 ± 0.51[a] | 4.74 ± 0.46††  |
| IV. 0.5% cholesterol diet + lignan complex | 4.65 ± 0.27[a] | 5.02 ± 0.74 | 5.09 ± 0.56 |

*$P < 0.05$, 0 month vs 1 and 2 months in the respective groups.
†$P < 0.05$, 1 month vs 2 months in the respective group.
[a]$P < 0.05$, Group I vs other groups.
[b]$P < 0.05$, Group II vs Group III or Group IV.

TABLE 12

Monocyte Counts in the Blood ($10^9$/L) in the Experimental Groups

| | Time (months) | | |
|---|---|---|---|
| Group | 0 | 1 | 2 |
| I. Control diet | 0.56 ± 0.07 | 0.46 ± 0.05 | 0.28 ± 0.07* |
| II. Control diet + lignan complex | 0.62 ± 0.07 | 0.58 ± 0.047 | 0.33 ± 0.08*,† |
| III. 0.5% cholesterol diet | 0.75 ± 0.07 | 0.75 ± 0.08[a] | 0.37 ± 0.05*,† |
| IV. 0.5% cholesterol diet + lignan complex | 0.45 ± 0.05[c] | 0.56 ± 0.09 | 0.45 ± 0.02[a] |

*$P < 0.05$, "0" month vs 1 month and 2 months in the respective groups.
†$P < 0.05$, 1 month vs 2 months in the respective group.
[a]$P < 0.05$, Group I vs other groups.
[c]$P < 0.05$, Group III or Group IV.

TABLE 13

Platelet Counts in the Blood ($10^9$/L) in the Blood of Various Experimental Groups

| | Time (months) | | |
|---|---|---|---|
| Group | 0 | 1 | 2 |
| I. Control diet | 393 ± 46 | 324 ± 52 | 286 ± 25* |
| II. Control diet + lignan complex | 329 ± 20 | 280 ± 8* | 267 ± 23 |
| III. 0.5% cholesterol diet | 422 ± 24[b] | 341 ± 26* | 401 ± 31[a,b] |

TABLE 13-continued

Platelet Counts in the Blood ($10^9$/L) in the Blood of Various Experimental Groups

| | Time (months) | | |
|---|---|---|---|
| Group | 0 | 1 | 2 |
| IV. 0.5% cholesterol diet + lignan complex | 403 ± 20[b] | 309 ± 23* | 364 ± 37 |

*$P < 0.05$, "0" month vs other months in the respective groups.
[a]$P < 0.05$, Group I vs other groups.
[b]$P < 0.05$, Group II vs Group III or Group IV.

TABLE 14

Mean Platelet Volume in Fentoliter (fl) for Various Experimental Groups

| | Time (months) | | |
|---|---|---|---|
| Group | 0 | 1 | 2 |
| I. Control diet | 5.38 ± 0.27 | 5.64 ± 0.21 | 5.69 ± 0.21 |
| II. Control diet + lignan complex | 6.03 ± 0.16 | 5.81 ± 0.11 | 5.75 ± 0.11 |
| III. 0.5% cholesterol diet | 5.37 ± 0.07[a] | 5.27 ± 0.09[a] | 5.96 ± 0.11*,† |
| IV. 0.5% cholesterol diet + lignan complex | 5.51 ± 0.7[a] | 5.47 ± 0.07[a] | 5.85 ± 0.11*,† |

*$P < 0.05$, "0" month vs other months in the respective groups.
†$P < 0.05$, 1 month vs 2 months in the respective groups.
[a]$P < 0.05$, Group I vs other groups.
[b]$P < 0.05$, Group II vs Group III or Group IV.

TABLE 15

Serum Alkaline Phosphatase (ALP) Levels (U/L) in the Experimental Groups

| | Time (months) | | |
|---|---|---|---|
| Group | 0 | 1 | 2 |
| I. Control diet | 121.3 ± 20.2 | 152.6 ± 10.9 | 118.1 ± 7.7† |
| II. Control diet + lignan complex | | | 71.0 ± 9.65[a] |
| III. 0.5% cholesterol diet | 169.1 ± 16.6 | 191.5 ± 15.6 | 160.3 ± 11.6[a,b] |
| IV. 0.5% cholesterol diet + lignan complex | 142.7 ± 1.4 | 181.2 ± 7.9* | 132.7 ± 19.5 |

*$P < 0.05$, "0" month vs 1 month and 2 months in the respective groups.
†$P < 0.05$, 1 month vs 2 months in the respective group.
[a]$P < 0.05$, Group I vs other groups.
[b]$P < 0.05$, Group II vs Group III and Group IV.

TABLE 16

Serum Alanine Aminotransferase (ALT) Levels (U/L) in the Experimental Groups

| | Time (months) | | |
|---|---|---|---|
| Group | 0 | 1 | 2 |
| I. Control diet | 27.25 ± 3.6 | 44.2 ± 5.85 | 41.2 ± 3.5* |
| II. Control diet + lignan complex | Not measured | Not measured | 47.33 ± 9.2 |
| III. 0.5% cholesterol diet | 41.22 ± 3.1[a] | 59.3 ± 11.2 | 69.08 ± 13.3 |

TABLE 16-continued

Serum Alanine Aminotransferase (ALT) Levels (U/L) in the Experimental Groups

| Group | Time (months) | | |
|---|---|---|---|
| | 0 | 1 | 2 |
| IV. 0.5% cholesterol diet + lignan complex | 41.6 ± 2.6[a] | 45.4 ± 9.4 | 39.1 ± 5.6 |

*$P < 0.05$, "0" month vs other months in the respective groups.
[a]$P < 0.05$, Group I vs other groups.

TABLE 17

Serum Aspartate Aminotransferase (AST) Levels (U/L) in the Experimental Groups

| Group | Time (months) | | |
|---|---|---|---|
| | 0 | 1 | 2 |
| I. Control diet | 25.0 ± 5.1 | 25.4 ± 0.5 | 41.1 ± 3.6*,† |
| II. Control diet + lignan complex | Not measured | Not measured | 34.7 ± 4.4 |
| III. 0.5% cholesterol diet | 35.0 ± 3.3 | 44.1 ± 6.5 | 53.1 ± 2.4*,a |
| IV. 0.5% cholesterol diet + lignan complex | 28.8 ± 4.4 | 29.6 ± 2.4 | 49.4 ± 4.5*,† |

*$P < 0.05$, "0" month vs 1 month and 2 months in the respective groups.
†$P < 0.05$, 1 month vs 2 months in the respective group.
[a]$P < 0.05$, Group I vs other groups.

TABLE 18

Serum Levels (U/L) of Gamma-glutamyltransferase (GGT) in the Experimental Groups

| Group | Time (months) | | |
|---|---|---|---|
| | 0 | 1 | 2 |
| I. Control diet | 9.0 ± 0.8 | 8.8 ± 1.0 | 8.0 ± 1.9 |
| II. Control diet + lignan complex | Not measured | Not measured | 8.0 ± 1.3 |
| III. 0.5% cholesterol diet | 9.6 ± 0.4 | 8.6 ± 0.8 | 6.4 ± 1.7 |
| IV. 0.5% cholesterol diet + lignan complex | 9.0 ± 1.1 | 6.5 ± 0.6 | 6.4 ± 1.2 |

TABLE 19

Serum Albumin Levels (gm/L) in the Experimental Groups

| Group | Time (months) | | |
|---|---|---|---|
| | 0 | 1 | 2 |
| I. Control diet | 15.8 ± 0.2 | 17.8 ± 0.37* | 30.3 ± 5.2 |
| II. Control diet + lignan complex | | | 35.50 ± 4.52 |
| III. 0.5% cholesterol diet | 16.9 ± 0.31 | 18.3 ± 0.42* | 20.41 ± 2.58 |
| IV. 0.5% cholesterol diet + lignan complex | 17.2 ± 0.2 | 19.0 ± 0.54* | 26.77 ± 4.1 |

*$P < 0.05$, comparison of the values at various times with respect to "0" time in the respective groups.

TABLE 20

Serum Creatinine Levels (μmoles/L) in the Experimental Groups

| Group | Time (months) | | |
|---|---|---|---|
| | 0 | 1 | 2 |
| I. Control diet | 48.4 ± 2.46 | 78.8 ± 2.35* | 103.3 ± 5.4*,† |
| II. Control diet + lignan complex | Not measured | Not measured | 104.25 ± 6.2* |
| III. 0.5% cholesterol diet | 62.12 ± 1.68[a] | 80.7 ± 3.9* | 106.4 ± 4.6*,† |
| IV. 0.5% cholesterol diet + lignan complex | 60.0 ± 6.0 | 73.2 ± 3.7 | 97.56 ± 5.33*,† |

*$P < 0.05$, comparison of values at various times with respect to "0" time in the respective groups.
†$P < 0.05$, 1 month vs 2 months in the respective group.
[a]$P < 0.05$, Group I vs other groups.

Since lignan complex lowers serum cholesterol, elevates serum HDL-C and reduces hypercholesterolemic atherosclerosis it will be of use in the prevention and treatment of the following diseases:

i) Hypercholesterolemic atherosclerosis.
ii) Coronary artery disease (heart attack).
iii) Stroke.
iv) Restenosis following percutaneous transluminal coronary angioplasty.
v) Restenosis after stent implant.
vi) Stroke, heart attack, renal failure and retinopathy in diabetes mellitus.
vii) Hypercholesterolemia.
viii) Peripheral vascular diseases, such as intermittent clandication.

The use of lignan complex derived from flaxseed according to this invention has the following advantages:

i) Lignan complex contains materials that have antioxidant and anti-PAF activity and hence is an anti-inflammatory agent.
ii) It lowers serum cholesterol, raises HDL-C and reduces hypercholesterolemic atherosclerosis.
iii) This compound is a natural food product and has no toxicity on hemopoietic system, liver and kidney, and it is a safe drug.
iv) It is inexpensive and safe as compared to other drugs used for lowering lipids and reducing atherosclerosis.
v) This compound is cheaper than SDG because processing of SDG is expensive as compared to lignan complex.
vi) The dose of lignan complex is very small as compared to flaxseed.

What is claimed is:

1. A method for treating hypercholesterolemic atherosclerosis or for reducing total cholesterol while raising high-density lipoprotein cholesterol which comprises administering to a patient an effective amount of a complex having a purity of at least 95% derived from flaxseed and containing about 34 to 37% by weight secoisolariciresinol diglucoside (SDG), about 13 to 21% by weight cinnamic acid glucosides and about 9.6 to 11.0% by weight hydroxymethyl glutaric acid.

2. A method according to claim 1 wherein the cinnamic acid glucosides include coumaric acid glucoside and ferulic acid glucoside.

* * * * *